Figure 1:
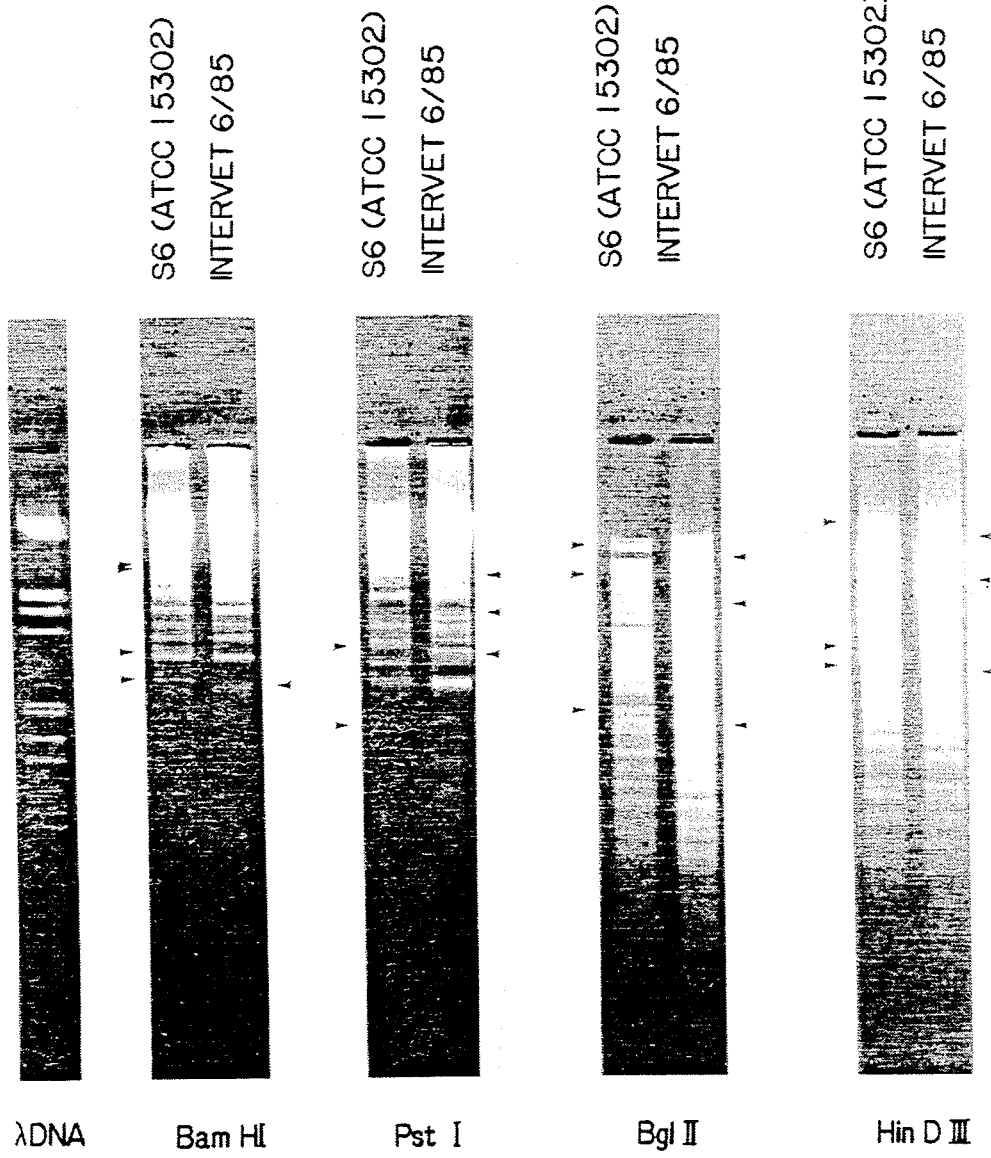

United States Patent [19]

Storm

[11] Patent Number: 5,064,647
[45] Date of Patent: Nov. 12, 1991

[54] MYCOPLASMA VACCINE

[75] Inventor: Paul K. Storm, Boxmeer, Netherlands

[73] Assignee: Akzo N.V., Arnhem, Netherlands

[21] Appl. No.: 231,913

[22] Filed: Aug. 12, 1988

[30] Foreign Application Priority Data

Sep. 18, 1987 [NL] Netherlands ............... 8702232

[51] Int. Cl.$^5$ .................. A61K 39/02; C12N 1/00
[52] U.S. Cl. ......................... 424/92; 424/88; 435/240.1; 435/240.2; 435/243; 435/245
[58] Field of Search ............. 424/92, 88; 435/240.1, 435/240.2, 243, 245

[56] References Cited

FOREIGN PATENT DOCUMENTS 52-134019 9/1977 Japan .

OTHER PUBLICATIONS

Lin et al., Avian Dis. vol. 28(1): pp. 88–99, 1984.
Lin et al., J. Chim. Soc. Vet. Sci., vol. 12(4), pp. 311–322, 1987.
Karaca et al., Avian Dis., 30(4), pp. 772–775, 1986.
Soeripto et al., Aust. Vet. J. vol. 66(3) pp. 73–77, 1989.

*Primary Examiner*—Margaret Moskowitz
*Assistant Examiner*—Abdel A. Mohamed
*Attorney, Agent, or Firm*—William M. Blackstone

[57] ABSTRACT

The present invention is concerned with a novel Mycoplasma vaccine which is avirulent for chickens and is not pathogenic for turkeys. In particular such vaccine contains the Mycoplasma strain Intervet 6/85 (deposit No. I-673 at CNCM, Pasteur Institute, Paris France).

8 Claims, 1 Drawing Sheet

MYCOPLASMA VACCINE

The invention relates to a mycoplasma vaccine and to a method for protecting poultry against mycoplasma infections by administering such a vaccine.

Mycoplasma, and more particularly, *M. gallisepticum*, is a bacterium which is infectious, in particular, for poultry. The infection of commercially important birds with said bacterium causes appreciable economic losses.

The syndrome which *M. gallisepticum* causes is usually termed in the case of chickens "chronic respiratory disease" and in the case of turkeys "infectious sinusitis". The *M. gallisepticum* infection is often also accompanied with infection due to respiratory viruses and due to *Escherichia coli*.

*M. gallisepticum* infections can be combated with certain antibiotics, such as erythromycin, streptomycin, chlorotetracyclin, tylosin and magnamycin, which are usually mixed with the feed, but the bacteria are developing resistances to said substances to an increasing extent, as a result of which combating is becoming increasingly difficult.

Vaccines have been developed for the immunological protection of poultry against *M. gallisepticum* infections.

Inactivated *M. gallisepticum* bacterins have been used with varying result. Although these resulted in a good serological response, especially when administered in combination with an oil-emulsion adjuvant, such vaccines did not appear to protect against infections.

In a limited number of states of the USA, especially in the so-called "multiple-age egg-laying farms" vaccination was carried out with weakened live *M. gallisepticum* of the F-strain. Said strain is administered by the spray method and provides a reasonable protection against air sac inflammations, and reduces the drop in egg production to an acceptable level.

The disadvantages of the known inactivated vaccines are innumerable. Each animal has to be injected individually. The vaccine is very expensive. The animals are not protected against infection, i.e. after infection they may remain carriers of the (virulent) mycoplasma.

Even the existing live vaccines are not without problems. Although the F-strain is fairly avirulent for chickens, it is very pathogenic for turkeys. In addition, after the vaccination, the chickens remain carriers of the vaccine strain which can thus also continue to spread for a prolonged period.

An *M. gallisepticum* vaccine has now been found which does not have the drawbacks referred to above.

The mycoplasma vaccine according to the invention is characterized in that it is derived from a *M. gallisepticum* strain which has the immunological properties of the Intervet 6/85 strain.

The Intervet 6/85 strain is a new *M. gallisepticum* strain, a mutant which has been obtained by a number of "in vitro" passages of the known S6 strain (ATCC No. 15302).

This new strain, which was deposited with the Collection Nationale de Cultures de Microorganismes of the Pasteur Institute in Paris 25 Rue du Docteur Roux, 75724 Paris Cedex 15, on 7th July 1987 under number I-673, therefore also belongs to the invention. Strains which have the same characteristic immunological properties as the said Intervet 6/85 strain also belong to the invention. More particularly, strains which, while retaining the particularly favorable immunological properties, are derived from the Intervet 6/85 strain also belong to the invention.

The Intervet 6/85 strain has a number of important advantages over the known *M. gallisepticum* strains which make it extremely suitable for vaccine applications and which also distinguish it from the known *M. gallisepticum* strains:

a. not virulent for chickens: no clinical symptoms at all; air sac inflammations virtually do not occur;
b. not virulent for turkeys;
c. 4 weeks after administration is still found only in a negligible number of animals, while the F-strain continues to be secreted for a long time by almost 100% of the animals;
d. an endonuclease restriction pattern as shown in FIG. 1.

The vaccine according to the invention is preferably administered to poultry in the form of a live vaccine, although it can, however, also be used as an inactivated vaccine.

The mycoplasma vaccine can be administered in the manner usual for similar vaccines, but the present vaccine lends itself, in particular, to administration as an aerosol. Very finely divided aerosols of the vaccine may, for example, be prepared by means of a Vineland aerosol apparatus.

The mycoplasma vaccine according to the invention may be marketed, for example, in freeze dried form. From this, a suspension can be prepared by adding an aqueous liquid, for example tapwater. The vaccine can, of course, also be marketed as a suspension. If desired, in addition to the mycoplasma material, one or more stabilizers (such as skimmed milk or casein hydrolysate) and/or one or more antibiotics (such as ampicillin or polymyxin) may be present in the vaccine.

The present vaccine is suitable for combating mycoplasma infections in poultry. In particular, it is suitable for combating mycoplasma infections in chickens and turkeys. The vaccine can best be administered in the rearing period, preferably at an age of 8-15 weeks, as a protection against a fall in production during the laying period. Vaccination should be carried out preferably in the rearing period because:

a. a slight inoculation reaction which might result from the vaccination has no effect on the egg production at this stage;
b. the protection must be adequate at the instant when the animals begin to lay;
c. the animals should be protected when they are transferred from the rearing farm to the laying farm where the infection usually takes place.

One of the favorable characteristics of the vaccine according to the invention is its very low virulence for chickens.

This was demonstrated in white Leghorn breeders, in which the effects of the Intervet 6/85 strain, the R-strain and the F-strain were compared. The R-strain is regarded as a very virulent *M. gallisepticum* strain. The F-strain is used in the USA as a vaccine strain. Both strains were made available by S. Kleven of the University of Georgia. The R- and F-strains were cultured in the media described by Frey et al. (M. C. Frey, R. P. Hanson and D. P. Anderson (1968) Amer.J.Vet. Res. 29, 2164–71), while the Intervet 6/85 strain was cultured in a modified Adler medium (H. E. Adler, R. Yamamoto and S. Bankowski, (1954) Amer.J.Vet.Res 15, 463–5). The modifications of the Adler medium consisted in replacing Bacto PPLO broth by protease peptone and horse serum by porcine serum.

The chickens used in these comparative experiments had previously been found seronegative both for *M. gallisepticum* and for M. synoviae.

Approximately a week before the experiments, 10 chickens were placed in a reduced-pressure isolator. Mycoplasma was administered to these chickens by the aerosol method. 100 ml of the respective mycoplasma culture was atomized for 10 minutes in the isolator, the air exhaust from which had been cut off. The Intervet 6/85 suspension administered contained $10^{10}$ viable organisms per ml, While both the F- and R-strain suspension contained only $10^8$ viable organisms per ml.

A post mortem examination was carried out 10 and 24 days after administrating mycoplasma—in both cases with 5 chickens. The chickens were examined in relation to air sac damage, ovary degeneration and the number of animals from which *M. gallisepticum* can be isolated. The results were reproduced as described in Example 2 under a, b, and c respectively.

The results are reproduced in the tables below.

| Administered | Days after administration | Air sac damage | Ovary degeneration | Reisolation (%) |
|---|---|---|---|---|
| Infection of 27-week-old chickens ||||
| R-strain | 10 | 3.0 | 3.0 | 100 |
| Intervet 6/85 | 10 | 0.6 | 0.2 | 40 |
| — | | 0.0 | 0.0 | 0 |
| R-Strain | 24 | 1.0 | 0.6 | 100 |
| Intervet 6/85 | 24 | 0.0 | 0.2 | 40 |
| — | | 0.0 | 0.0 | 0 |
| Infection of 32-week-old chickens ||||
| R-strain | 10 | 3.2* | 2.5 | 100 |
| Intervet 6/85 | 10 | 0.3 | 0.8 | 17 |
| — | | 0.0 | 0.0 | 0 |
| Infection of 35-week-old chickens ||||
| R-strain | 10 | 2.8 | 2.6 | 100 |
| Intervet 6/85 | 10 | 0.2 | 1.4 | 20 |
| F-strain | 10 | 2.0 | 1.6 | 100 |
| — | | 0.0 | 0.1 | 0 |
| R-Strain | 24 | 0.6 | 0.8 | 100 |
| Intervet 6/85 | 24 | 0.0 | 0.0 | 0 |
| F-strain | 24 | 0.6 | 0.4 | 80 |
| — | | 0.0 | 0.0 | 0 |
| Infection of 39-week-old chickens ||||
| R-strain | 10 | 2.2 | 2.4 | 100 |
| Intervet 6/85 | 10 | 0.0 | 0.8 | 0 |
| F-strain | 10 | 2.0 | 1.4 | 20 |
| — | 40-weeks-old) | 0.0 | 0.4 | 0 |

*average of 6 chickens

From the above data it emerges that the Intervet 6/85 strain causes appreciably less air sac and ovary damage than both the R- and F-strain.

In addition, it emerges that the Intervet 6/85 strain is no longer detectably present in the infected chickens after approximately 4 weeks, while both the R- and the F-strains could in fact often still be detected at that time.

Similar experiments have been done with 4-weeks-old white turkeys. The results are reproduced in the table below.

| Administered | Days after administration | Air sac damage | Reisolation (%) |
|---|---|---|---|
| R-strain | 10 | 3.2 | 100 |
| Intervet 6/85 | 10 | 0.2 | 100 |
| F-strain | 10 | 2.6 | 100 |
| — | (5¼ weeks old) | 0.4 | 0 |
| R-Strain | 28 | 3.75 | 100 |
| Intervet 6/85 | 28 | 0.5 | 0 |
| F-strain | 28 | 2.6 | 100 |
| — | (8 weeks old) | 0.2 | 0 |

Turkeys are known to be particularly susceptible to *M. gallisepticum*, even to relatively low-virulent strains, such as the F-strain, which is used as a vaccine strain in the case of chickens.

The above results demonstrate, however, that the new Intervet 6/85 strain is also of very low virulence for turkeys and produces virtually no damage.

The Intervet 6/85 strain was also investigated for reversion to virulence. For this purpose, the strain was passaged 5 times through chickens, the mycoplasma reisolated by means of "tracheal swab" being administered each time to the new chickens. The results are reproduced in the table below. No increase in the virulence was found even after 5 passages.

| Administered | Passage No. | Days after administration | Age (weeks) | Air sac damage | Ovary degeneration | Reisolation (%) |
|---|---|---|---|---|---|---|
| Intervet 6/85 | 2 | 10 | 29 | 0.75 | 1.2 | 66 |
| — | | | 29 | 0.25 | 0.0 | 0 |
| Intervet 6/85 | 3 | 10 | 35 | 0.0 | 1.0 | 20 |
| Intervet 6/85 | 0 | 10 | 35 | 0.2 | 1.4 | 20 |
| R-strain | 0 | 10 | 35 | 2.8 | 2.6 | 100 |
| — | | | 35 | 0.0 | 0.1 | 0 |
| Intervet 6/85 | 4 | 10 | 39 | 0.4 | 1.4 | 20 |
| Intervet 6/85 | 0 | 10 | 39 | 0.0 | 0.8 | 0 |
| R-strain | 0 | 10 | 39 | 2.2 | 2.4 | 100 |
| — | | | 39 | 0.0 | 0.4 | 0 |
| Intervet 6/85 | 5 | 10 | 41 | 0.4 | 1.4 | 20 |
| R-strain | 0 | 10 | 41 | 2.2 | 2.2 | 100 |
| — | | | 41 | 0.0 | 0.4 | 0 |

EXAMPLE 1

Preparation of a live vaccine

A quantity of approximately 1 ml of seed material of the Intervet 6/85 strain of *Mycoplasma gallisepticum* is reconstituted in 10 ml of modified Adler medium and incubated at 37° C.

When sufficient growth had taken place, which was assessed on the basis of the change in color of an indicator which had been added (phenol red), the suspension is inoculated into a freshly modified Adler medium in a volume ratio of 1:20 and incubated again in the manner described above.

This scaling up is repeated until an inoculum is obtained which is large enough to inoculate the fermenter to be used (approximately 5 l of inoculum is necessary for a 100 l fermenter).

After inoculating the fermenter, incubation is carried out for 24–30 hours at a pH of 7.5, a temperature of 37° C. and with a constant stirring speed and aeration.

Then the cells are collected by centrifuging and taken up in skimmed milk (10%) to which ampicillin has been added.

After being filled into suitable phials, the vaccine is freeze-dried and the phials are then sealed.

EXAMPLE 2

Vaccination experiments with chickens

Two groups of 10 chickens were vaccinated by the aerosol method with respectively the F-strain and the Intervet 6/85 strain and placed in reduced-pressure isolators.

Two weeks later, the two groups and also an unvaccinated control group were infected with the virulent R-strain and killed 10 days later. The air sac damage, ovary degeneration and the relative quantity of *M. gallisepticum* present in the killed animals were determined in the manner described below:

a) The gradations in air sac damage were classified as follows:

0 = clear air sacs without lymphofollicular damage;
1 = slight turbidity in one of the two air sacs or lymphofollicular damage in one or two air sacs;
2 = as 1, but in this case in both air sacs, or intense turbidity in one or two air sacs, or cheese-like secretion on one or two air sacs, or one or two air sacs which have become thick and fleshy;
3 = both air sacs intensely turbid or a cheese-like secretion or thickened and fleshy;
4 = combination of the symptoms under 3.

b) The degree of ovary degeneration was classified as follows:

0 = active ovaries without degeneration;
1 = a few of the follicles in the ovary deqenerated;
2 = all the follicles degenerated and some With hemorrhages;
3 = all the follicles degenerated with hemorrhages.

c) A determination was made of the number of chickens from which *Mycoplasma qallisepticum* could be reisolated.

This was expressed in the percentage of the total number of chickens in the respective groups.

The results of the experiments described above after vaccination of chickens of various ages are described below.

| Group | Air sac damage | Ovary degeneration | Reisolation* (%) |
|---|---|---|---|
| I. Vaccination of 27-weeks-old chickens | | | |
| Intervet 6/85 vaccination plus R-strain infection | 1.0 | 0.5 | 80 |
| No vaccination, but R-strain infection | 3.0 | 2.8 | 100 |
| Intervet 6/85 vaccination, no infection with R-strain | 0.0 | 0.2 | 40 |
| No vaccination, no infection with R-strain | 0.0 | 0.0 | 0 |
| II. Vaccination of 35-weeks-old chickens | | | |
| Intervet 6/85 vaccination plus R-strain infection | 1.2 | 2.0 | 100 |
| F-strain vaccination plus R-strain infection | 1.0 | 1.0 | 100 |
| No vaccination, but R-strain infection | 2.4 | 2.6 | 100 |
| Intervet 6/85 vaccination, no infection | 0.0 | 0.0 | 0 |
| F-strain, vaccination, no infection | 0.6 | 0.4 | 80 |
| No vaccination, no infection | 0.0 | 0.0 | 0 |
| III. Vaccination of 39-weeks-old chickens | | | |
| Intervet 6/85 vaccination plus R-strain infection | 0.0 | 1.0 | 100 |
| F-strain vaccination plus R-strain infection | 1.4 | 1.4 | 80 |
| No vaccination, but R-strain infection | 2.2 | 2.2 | 100 |
| No vaccination, no infection | 0.0 | 0.4 | 0 |

*No distinction made between R-strain, F-strain and Intervet 6/85 strain.

From these experiments it may be concluded that the Intervet 6/85 strain provides a protection against air sac damage and ovary degeneration as a consequence of a serious infection which is comparable with the protection which is obtained with the F-strain.

I claim:

1. Vaccine for combating mycoplasma infection in poultry, comprising an amount of *Mycoplasma gallisepticum* strain effective to protect poultry against *Mycoplasma gallisepticum* infection which is as protective against *Mycoplasma gallisepticum* as the Intervet 6/85 strain, CNCM number I-673, and a pharmaceutical acceptable carrier.

2. Vaccine according to claim 1, comprising a live *Mycoplasma gallisepticum* strain which has the immunological properties of the Intervet 6/85 strain.

3. An essentially biologically pure culture of a *Mycoplasma gallisepticum* strain which has the immunological properties of the Intervet 6/85 strain, CNCM number I-673.

4. An essentially biologically pure culture of a *Mycoplasma gallisepticum* strain Intervet 6/85, CNCM number I-673.

5. Method for combating mycoplasma infection in poultry, comprising administering a single vaccine according to claim 1 at an age of about 8-15 weeks.

6. Vaccine according to claim 1, comprising the Intervet 6/85 strain.

7. Method for combating mycoplasma infection in poultry, comprising administering a single vaccine according to claim 2 at an age of about 8-15 weeks.

8. A freeze dried vaccine according to claim 1.

* * * * *